United States Patent
Shuai et al.

(10) Patent No.: US 11,975,221 B2
(45) Date of Patent: May 7, 2024

(54) ANTI-MICROBIAL MULTILAYER FABRIC MEDIA AND METHOD FOR MAKING SAME

(71) Applicants: Danmeng Shuai, Herndon, VA (US); Yun Shen, Herndon, VA (US); Braydon McCormick, Old Lyme, CT (US)

(72) Inventors: Danmeng Shuai, Herndon, VA (US); Yun Shen, Herndon, VA (US); Braydon McCormick, Old Lyme, CT (US)

( * ) Notice: Subject to any disclaimer, the term of this patent is extended or adjusted under 35 U.S.C. 154(b) by 0 days.

(21) Appl. No.: 17/648,013

(22) Filed: Jan. 14, 2022

(65) Prior Publication Data

US 2022/0219027 A1 Jul. 14, 2022

Related U.S. Application Data

(60) Provisional application No. 63/201,247, filed on Apr. 20, 2021, provisional application No. 63/199,641, filed on Jan. 14, 2021.

(51) Int. Cl.

| | |
|---|---|
| A62B 23/02 | (2006.01) |
| A61L 9/16 | (2006.01) |
| B01D 69/12 | (2006.01) |
| F24F 8/108 | (2021.01) |
| F24F 8/24 | (2021.01) |
| F24F 8/90 | (2021.01) |
| A61L 101/02 | (2006.01) |

(52) U.S. Cl.
CPC ............ *A62B 23/025* (2013.01); *A61L 9/16* (2013.01); *B01D 69/12* (2013.01); *F24F 8/108* (2021.01); *F24F 8/24* (2021.01); *F24F 8/90* (2021.01); *A61L 2101/02* (2020.08); *A61L 2209/14* (2013.01)

(58) Field of Classification Search
CPC .......... F24F 8/90; A62B 23/025; B01D 69/12
See application file for complete search history.

(56) References Cited

U.S. PATENT DOCUMENTS

| | | | | |
|---|---|---|---|---|
| 3,613,678 A | * | 10/1971 | Mayhew | A41D 13/1115 128/206.19 |
| 2010/0151756 A1 | * | 6/2010 | Kim | D03D 15/587 442/3 |
| 2016/0220966 A1 | * | 8/2016 | Kano | B01D 69/02 |

FOREIGN PATENT DOCUMENTS

CN 102652028 A * 8/2012 ........... A61K 31/655

* cited by examiner

*Primary Examiner* — Robert A Hopkins
(74) *Attorney, Agent, or Firm* — Slavitt IP Law, LLC

(57) ABSTRACT

The present disclosure relates to a multilayer fabric media comprising a non-woven membrane of fibers comprising at least one polymer in combination with at least one photo-reactive agent mounted on a woven or non-woven substrate and coated with a light transmissible protective layer, to methods of forming such multilayer fabric media, and to articles of manufacture made therewith.

20 Claims, No Drawings

ANTI-MICROBIAL MULTILAYER FABRIC MEDIA AND METHOD FOR MAKING SAME

CROSS-REFERENCE TO RELATED APPLICATIONS

This patent application claims the benefit of U.S. Provisional Application Ser. No. 63/199,641 filed Jan. 14, 2021, and U.S. Provisional Application Ser. No. 63/201,247 filed Apr. 20, 2021. Both of the above applications are incorporated by reference herein.

STATEMENT OF GOVERNMENT-FUNDED RESEARCH

This invention was made with U.S. government support under Contract Nos. CBET2029411 and CBET2028464 awarded by the National Science Foundation. The U.S. government has certain rights in this invention.

FIELD OF TECHNOLOGY

The present disclosure generally relates to antimicrobial multilayer fabric media comprising a non-woven membrane of extruded or spun fibers mounted between a woven or non-woven substrate and a light transmissible protective layer, to methods for forming such multilayer fabric media, and to articles of manufacture utilizing such media.

BACKGROUND

The survival of bacteria, fungi, and viruses in aerosols leads to the subsequent transmission of these pathogens to new hosts, and significantly contributes to their proliferation, which in turn considerably increases their threat to human health, especially by novel viruses such as SARS-CoV-2. As such, there exists an urgent need for antimicrobial materials for use in HVAC air filters and in personal protective equipment such as face masks and respirators.

SUMMARY OF THE INVENTION

In one aspect, provided herein are antimicrobial multi-layer fabric media comprising a non-woven membrane mounted on a woven or non-woven substrate and coated with a light-transmissible protective layer. In one embodiment, the membrane comprises spun or extruded fibers comprising at least one polymer in combination with at least one photoreactive agent. In such embodiment, the at least one polymer and the at least one photoreactive agent are combined together, with or without a solvent, and the resulting solution may then by extruded or spun into the non-woven membrane. In one embodiment, the at least one polymer comprises poly(vinylidene difluoride) (PVDF), and the at least one photoreactive agent comprises a dye such as rose Bengal, methylene blue, toluidine blue O, crystal violet, and/or riboflavin.

The fibers comprising the membrane may be formed by any of a variety of suitable techniques including extrusion, such as microextrusion and melt-blown or solution-blown extrusion, as well as spinning, such as electrospinning, centrifugal spinning, centrifugal electrospinning, and combinations thereof.

In forming the multi-layer fabric media, one surface of the non-woven membrane is adhered to a woven or non-woven substrate, and a light-transmissible protective layer is then applied to the other surface of membrane. In one embodiment, the substrate comprises polypropylene and the light transmissible protective layer comprises polypropylene, polyethylene, polystyrene, polyethylene terephthalate, polyvinyl chloride, polycarbonate, and/or polymethyl methacrylate.

In another aspect, the multi-layer fabric media may be formed into an air filter for a room air filtration system or building HVAC system, or into a face mask or respirator for personal use. When formed into air filters or face masks/respirators, the multi-layer fabric media provides aerosol rejection efficiency of at least about 99%, and preferably at least about 99.9%, while maintaining breathability of about 0.25 or less inches of water column when tested with a face velocity of 5.3 cm/s. Moreover, the at least one photoreactive agent incorporated in the membrane is capable of absorbing electromagnetic radiation and generating reactive oxygen species such as singlet oxygen, $^1O_2$, which is an oxidizing agent that can react with biomolecules causing oxidative damage. The ability of the photoreactive agent to generate singlet oxygen degrades over time, and this degradation results in a color change that acts as a visual indicator of usable life for articles made from the multi-layer fabric media.

DETAILED DESCRIPTION

In one aspect, provided herein are multilayer antimicrobial fabric media comprising a non-woven fiber membrane mounted on a woven or non-woven substrate, wherein the membrane fibers comprise at least one polymer in combination with at least one photoreactive agent. The non-woven fiber membrane may be coated with a light-transmissible protective layer.

The polymer component of the fiber may comprise one or more polymers including, without limitation, PVDF, polyvinyl acetate, poly(vinyl alcohol), poly(ethylene oxide), polycaprolactone, polylactic acid, polyacrylonitrile, nylon-6, polyethylene terephthalate, polyurethane, polyimide, poly(ethylene-co-vinyl alcohol), cellulose acetate, polyglycolic acid, or a copolymer of one or more of the foregoing. In one embodiment, the polymer component comprises PVDF or a PVDF copolymer such as PVDF-hexafluoropropylene.

The at least one polymer component is provided in an amount suitable for use in the various techniques for forming fibers microscale or nanoscale fibers. In certain embodiments, the polymer component may comprise from about 8 wt % to about 20 wt %. In one embodiment, the polymer component comprises about 15 wt %.

The at least one photoactivatable agent that may be used in forming the non-woven membrane includes, but is not limited to, the following:

Chlorophyll dyes including, but not limited to, chlorophyll a; chlorophyll b; chlorophyllin; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene dyes including, but not limited to, eosin, eosin B (4,5-dibromo,2',7'-dinitro-fluorescein, dianion); eosin Y (T,4,5',7'-tetrabromo-fluorescein, dianion); eosin (2',4,5',7'-tetrabromofluorescein, dianion); eosin (2',4,5',7'-tetrabromofluorescein, dianion) methyl ester; eosin (2',4,5',7'-tetrabromofluorescein, monoanion) p-isopropylbenzyl ester; eosin derivative (2',7'-dibromo-fluorescein, dianion); eosin derivative (4,5'-dibromo-fluorescein, dianion); eosin derivative (2',7'-dichloro-fluorescein, dianion); eosin derivative (4',5'-dichloro-fluorescein, dianion); eosin derivative (2',7'- diiodo-fluorescein, dianion); eosin derivative (4,5-diiodo-fluorescein, dianion); eosin derivative (tribromo-fluorescein, dianion); eosin derivative (2',4,5,7'-tetrachloro-fluorescein, dianion); eosin dicetylpyridinium chloride ion pair; erythrosin B (2',4,5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose Bengal (3,4,5,6-tetrachloro-T,4',5',7'-tetraiodofluorescein, dianion); pyronin G; pyronin J; and pyronin Y.

Rhodamine dyes including, but not limited to, 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene blue dyes including, but are not limited to, 1-methyl methylene blue; 1,9-dimethyl methylene blue; methylene blue; toluidine blue 0; methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Azo (or diazo-) dyes including, but not limited to, methyl violet, neutral red, para red (pigment red 1), amaranth (Azorubine S), Carmoisine (azorubine, food red 3, acid red 14), allura red AC (FD & C 40), tartrazine (FD & C Yellow 5), orange G (acid orange 10), Ponceau 4R (food red 7), methyl red (acid red 2), and murexide-ammonium purpurate.

Additional photoactivatable agents include porphyrin, protoporphyrin, hematoporphyrin, chlorin, purpurin, pheophorbide, bacteriopheophorbide, texaphyrin, bacteriochlorin, porphyrin related-phthalocyanine, and derivatives thereof.

In some aspects of the disclosure, the one or more photoreactive agents disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2, Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid, Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau R, Crystal violet, Dahlia, Diamond green B, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallo cyanin, Gentian violet, Haematein, Haematine, Haematoxylin, Helio fast rubin BBL, Helvetia blue, Hematein, Hematine, Hematoxylin, Hoffman's violet, Imperial red, Indocyanin Green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39, Naphthol blue black, Naphthol green B, Naphthol yellow S, Natural black 1, Natural green 3 (chlorophyllin), Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, Picric acid, Ponceau 2R, Ponceau 6R, Ponceau B, Ponceau de Xylidine, Ponceau S, Primula, Purpurin, Pyronin B, Phycobilins, Phycocyanins, Phycoerythrins, Phycoerythrincyanin (PEC), Phthalocyanines, Pyronin G, Pyronin Y, Quinine, Rhodamine B, Rosanilin, rose Bengal, Saffron, Safranin 0, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Vitamin B, Water blue 1, Water soluble eosin, Xylidine ponceau, or Yellowish eosin.

The photoreactive agent is provided in an amount sufficient to generate singlet oxygen when combined with the polymer component and formed into a non-woven membrane. Preferably, the photoreactive agent comprises about 0.003 wt % to about 0.3 wt %. In embodiments in which rose Bengal is used, the photoreactive agent preferably comprises about 0.3 wt %. In embodiments in which methylene blue is used, the photoreactive agent preferably comprises about 0.003 wt % to about 0.015 wt %. If photoreactive agents are used in combination, a mixture of different colors, e.g., a red and a blue dye may be preferred so that they use more of the available spectrum of white light.

The fibers comprising the non-woven membrane may be formed by any suitable technique for forming microscale or nanoscale polymer fibers. Such techniques include, without limitation, various forms of extrusion such as microextrusion, melt-blown extrusion, and solution-blown extrusion, as well as various forms of spinning, such as electrospinning, centrifugal spinning, and centrifugal electrospinning, and combinations thereof.

In embodiments in which membrane fibers are spun, the polymer component and the photoreactive agent may be combined with or without a solvent. When a solvent is used, the solvent may be any solvent suitable for use in spinning the polymer component and the photoreactive agent including, without limitation, acetone, acetonitrile, alcohol, aniline, n-butyl acetate, chloroform, chloromethane, cyclohexanone, diacetone, dichloromethane, diethylene glycol, dimethylacetamide, dimethylformamide, dimethylsulfoxide, ethanediol, ethanol, 2-ethoxyethanol, 2-ethoxyethyl acetate, ethyl acetate, ethylene dichloride, glycerol, isopropanol, methanol, methyl acetate, methylene chloride, N-methyl-2-pyrrolidone, monoethyl ether, morpholine, 2-nitropropane, 1-pentanol, n-propanol, propylene carbonate, tetrachloroethane, tetrahydrofuran, and water.

In certain embodiments, a homogenous mixture of the polymer component and photoreactive agent may be formed by any suitable means including, but not limited to, magnetic mixing, overhead mechanical mixing, and/or ultrasonication. Further, the homogeneity of the mixture of the polymer component and photoreactive agent may be facilitated by heating. In certain embodiments, the resulting solution has a polymer concentration of about 8 wt % to about 20 wt %.

If membrane fibers are formed by electrospinning, the flow rate is preferably between from about 0.1 to about 2 mL/h$^{-1}$, and the electric field strength is preferably between about 1 to about 5 kV/cm$^{-1}$. In one embodiment, the tip-to-collector distance is about 10 to about 20 cm, and a blunt needle tip with 18-30 gauge is used. A plate or rotating drum may be used to collect the electrospun fibers. If a rotating drum is used, the rate of rotation is preferably from about 100 to about 1000 rpm. Ambient conditions for electrospinning may be normal room temperature and room humidity, but may vary from between about 10° C. to about 40° C., and from about 10% to about 70% relative humidity.

Insofar as electrospinning is conducted under a strong electric field, the electrospun fibers produced thereby exhibit retained surface and volume charges that can last for weeks or even months. The presence of such retained charges can significantly promote aerosol capture through electrostatic attraction.

In certain embodiments, the flow rate of the solution, electric field, and duration is at 0.6 mL h$^{-1}$, 1 kV cm$^{-1}$, and 20 or 30 min respectively. The resulting electrospun membranes are designated as PVDF$_{20}$ and PVDF$_{30}$, respectively.

Force or centrifugal spinning is a process that spins fibers of diameters ranging from 10 nm to several hundred nanometers using a rotary drum and a nozzle, much like a cotton candy machine. The process makes use of a combination of hydrostatic and centrifugal pressure to spin fibers from the nozzle. For example, one type of centrifugal spinning is rotary jet spinning, where a polymeric material is retained inside a reservoir atop a controllable motor and extruded out of a rapidly rotating nozzle or spinneret. Centrifugal spinning can make nanofibers either from polymers in solvents or by using molten polymers. Centrifugal spinning and electrospinning can also be combined. In such embodiments, the assistance of centrifugal forces allow for electrospinning of polymer fibers using a weaker electric field.

In one embodiment, the spinneret can comprise a syringe and plunger or other extruding structure having one or more openings through which the polymeric material can be forced, wherein when the spinneret (and its tip opening) is configured to rotate about a spin axis. An apparatus for force spinning fibers generally employs centrifugal forces to transform material into fibers. Such apparatus is described in detail in the following U.S. Published Patent Applications, and the references cited therein: US Patent Publications 2009/0269429; 2009/0280325; 2014/0035178; and 2014/0035179, all of which are hereby incorporated by reference in their entireties.

In a force-spinning fiber-producing system, the fibers may be laid down on a substrate surface perpendicular to the axis of rotation, and the spread of the fibers can be controlled such that the deposited fibers are as uniform as possible across the deposition width. Several system parameters influence, and can be adjusted, to control the spread of fibers. For example, rotational velocity, air flow through the system, and distance between the one or more openings, from which the fiber composition is extruded, and the specific collection substrate are among the system parameters than can be readily modified.

In certain embodiments, membrane fibers may have a diameter of from about 50 nm (+/−20 nm) to about 1000 nm (+/−200 nm). In one embodiment, membrane fibers may be straight. In another embodiment, membrane fibers may be straight with beads at either regular or irregular intervals.

To increase binding of aerosol particulates by electrostatic attraction and to promote aerosol removal efficiency, a positive or negative charged polyelectrolyte, such as poly (ethyleneimine) or poly(vinylphosphonic acid), may be coated onto the membrane fibers.

In certain embodiments, the average pore size of the non-woven membrane may range from about 100 nm to about 200 nm for membranes comprising fibers having an average diameter of about 50 nm, to about 3-5 microns for membranes comprising fibers having an average diameter of about 1000 nm. In embodiments in which the average fiber diameter is about 500 nm, the average pore size is about 2 μm to about 3 μm (+/−0.2-0.3 μm). In certain embodiments, the membrane has a thickness of about 10 to about 1000 microns.

In certain embodiments, the membrane fiber diameter of PVDF$_{20}$, PVDF$_{30}$, PVDF$_{20}$/PEI, and PVDF$_{20}$/PVPA range from about 0.2 μm to about 1.3 μm. Increase of spinning duration and thickness of the spun membrane can enhance viral aerosol removal (99.9% and 99.1% for PVDF$_{30}$ and PVDF$_{20}$, respectively. Average viral filtration efficiency for PVDF$_{20}$/PEI and PVDF$_{20}$/PVPA is 99.1% and 95.7%, respectively.

The photoreactive agent in the non-woven membrane produces singlet oxygen in the presence of electromagnetic radiation. In one embodiment, the photoreactive agent in the membrane produces sufficient singlet oxygen resulting in at least 95% genome damage of coronaviruses after 1 hour of white LED light exposure. In another embodiment, the photoreactive agent in the membrane produces sufficient singlet oxygen resulting in at least 99.9% coronavirus inactivation after 30 min of white LED light exposure. Over a period of light exposure, the color imparted by the photoreactive agent fades. As a result, this color change can serve as an indicator of photosensitizer concentration and antimicrobial effectiveness of the multilayer media.

In forming the antimicrobial multilayer media, the membrane is secured to a compatible woven or non-woven substrate having a permeability at least as high as the membrane. The attachment of the membrane to the substrate may be accomplished by a variety of methods including, without limitation, stitching, gluing, taping, clamping, heat fusing, and laser melting.

In one embodiment, the substrate may comprise polypropylene. In other embodiments, the substrate comprises a cotton, nylon, or polyester fabric. In one embodiment, the substrate comprises a combination of natural and/or synthetic fabrics, or at least one fabric comprising a blend of natural and/or synthetic fibers. In one embodiment, the substrate has anti-static properties and/or is combined with an additional anti-static component.

The multilayer media is also provided with a protective layer having a permeability at least as high as the non-woven membrane and a light transmissibility of at least about 50%. The protective layer may comprise any material having such properties including, without limitation, polyethylene, polystyrene, polyethylene terephthalate, polyvinyl chloride, polycarbonate, and/or polymethyl methacrylate.

The multilayer media of the present invention possesses a unique combination of properties that provide a high degree of breathability, aerosol rejection efficiency, and anti-microbial action. In one embodiment, the multilayer media exhibits 0.25 or less inches water column when measured at 5.3 cm/s of face velocity, and an aerosol rejection efficiency of at least 99%. The capacity of the multilayer media to produce singlet oxygen in the presence of electromagnetic radiation, such as visible light, provides superior antimicrobial properties. Moreover, the color change of the photoreactive agent component of the non-woven membrane layer provides a visual indicator of anti-microbial effectiveness as the production of singlet oxygen by the exposure of the membrane to electromagnetic radiation degrades over time. This unique combination of properties makes the multilayer media particularly suitable in the construction of room air filters, building HVAC system filters, and personal protective equipment such as face masks and respirators.

Variations and modifications will occur to those of skill in the art after reviewing this disclosure. The disclosed features may be implemented, in any combination and sub-combinations (including multiple dependent combinations and sub-combinations), with one or more other features described herein. The various features described above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

We claim:

1. A multilayer antimicrobial fabric media, comprising:
a substrate layer, and
a non-woven fiber membrane having a top surface and a bottom surface, wherein the bottom surface of the membrane is affixed to the substrate layer and wherein the membrane fibers comprise at least one polymer in combination with between 0.003 wt. % and 0.3 wt. % of at least one photoreactive agent capable of generating singlet oxygen in the presence of electromagnetic radiation.

2. The multilayer antimicrobial fabric media of claim 1, wherein the at least one polymer is selected from the group consisting of poly(vinylidene difluoride), polyvinyl acetate, poly(vinyl alcohol), poly(ethylene oxide), polycaprolactone, polylactic acid, polyacrylonitrile, nylon-6, polyethylene terephthalate, polyurethane, polyimide, poly(ethylene-co-vinyl alcohol), cellulose acetate, polyglycolic acid, and copolymers thereof.

3. The multilayer antimicrobial fabric media of claim 1, wherein the at least one polymer comprises poly(vinylidene difluoride).

4. The multilayer antimicrobial fabric media of claim 1, wherein the at least one polymer comprises a poly(vinylidene difluoride)-hexafluoropropylene copolymer.

5. The multilayer antimicrobial fabric media of claim 1, wherein the at least one photoreactive agent comprises a dye.

6. The multilayer antimicrobial fabric media of claim 5, wherein the dye is selected from the group consisting of rose Bengal, methylene blue, toluidine blue O, crystal violet, and riboflavin.

7. The multilayer antimicrobial fabric media of claim 5, wherein the dye is a xanthene dye.

8. The multilayer antimicrobial fabric media of claim 5, wherein the dye is rose Bengal.

9. The multilayer antimicrobial fabric media of claim 1, wherein the non-woven fiber membrane comprises fibers electrospun from a solution comprising the at least one polymer and at least one photoreactive agent.

10. The multilayer antimicrobial fabric media of claim 1, wherein the non-woven fiber membrane comprises fibers centrifugally spun from a solution comprising the at least one polymer and at least one photoreactive agent.

11. The multilayer antimicrobial fabric media of claim 1 further comprising a light-transmissible protective layer applied to the top surface of the membrane.

12. The multilayer antimicrobial fabric media of claim 11, wherein the light transmissible protective layer is selected from the group consisting of polypropylene, polyethylene, polystyrene, polyethylene terephthalate, polyvinyl chloride, polycarbonate, and polymethyl methacrylate.

13. An air filter, comprising:
a multilayer antimicrobial fabric media filter element, wherein the filter element comprises a non-woven fiber membrane mounted on a substrate layer and wherein the membrane fibers comprise at least one polymer in combination with between 0.003 wt. % and 0.3 wt. % of at least one photoreactive agent capable of generating singlet oxygen in the presence of electromagnetic radiation.

14. The air filter of claim 13, wherein filter element further comprises a light-transmissible protective layer applied to the membrane.

15. The air filter of claim 13, wherein the at least one polymer comprises poly(vinylidene difluoride) and wherein the at least one photoreactive agent comprises a xanthene dye.

16. A face mask, comprising:
a multilayer antimicrobial fabric media filter element, wherein the filter element comprises a non-woven fiber membrane mounted on a substrate layer wherein the membrane fibers comprise at least one polymer in combination with between 0.003 wt. % and 0.3 wt. % of at least one photoreactive agent capable of generating singlet oxygen in the presence of electromagnetic radiation.

17. The face mask of claim 16 wherein filter element further comprises a light-transmissible protective layer applied to the membrane.

18. The face mask of claim 16, wherein the at least one polymer comprises poly(vinylidene difluoride) and wherein the at least one photoreactive agent comprises a xanthene dye.

19. The face mask of claim 16, wherein the filter element has an average pore size of about 2 μm to about 3 μm to provide aerosol rejection efficiency of at least about 99% while maintaining breathability of about 0.25 or less inches of water column when tested with a face velocity of 5.3 cm/s.

20. The face mask of claim 16, wherein the at least one photoreactive agent imparts a color to the filter element that fades with exposure to light and wherein the color change is a visual indicator of a reduction in singlet oxygen generation.

* * * * *